(12) United States Patent
Mori et al.

(10) Patent No.: US 10,471,572 B2
(45) Date of Patent: Nov. 12, 2019

(54) ABRASIVE SHEET

(71) Applicant: Reckitt Benckiser (Brands) Limited, Slough (GB)

(72) Inventors: Yasuhiro Mori, Hull (GB); Peter Phillips, Hull (GB); Luke Shipman, Hull (GB); Peter Colin Formby, Sheffield (GB); Andrew Pryke, Sheffield (GB); Christopher Saywell, Sheffield (GB)

(73) Assignee: RECKITT BENCKISER HEALTH LIMITED, Slough (GB)

( * ) Notice: Subject to any disclaimer, the term of this patent is extended or adjusted under 35 U.S.C. 154(b) by 192 days.

(21) Appl. No.: 15/565,270

(22) PCT Filed: Apr. 11, 2016

(86) PCT No.: PCT/GB2016/051005
§ 371 (c)(1),
(2) Date: Oct. 9, 2017

(87) PCT Pub. No.: WO2016/162698
PCT Pub. Date: Oct. 13, 2016

(65) Prior Publication Data
US 2018/0056485 A1    Mar. 1, 2018

(30) Foreign Application Priority Data

Apr. 10, 2015 (GB) .................................. 1506092.4

(51) Int. Cl.
*B24D 3/34* (2006.01)
(52) U.S. Cl.
CPC .................................... *B24D 3/34* (2013.01)

(58) Field of Classification Search
CPC ........................................................ B24D 3/34
USPC ............................................................ 451/533
See application file for complete search history.

(56) References Cited

U.S. PATENT DOCUMENTS

| 81,986 | A | * | 9/1868 | Crane | ................. | B24D 11/00 |
|---|---|---|---|---|---|---|
| | | | | | | 451/533 |
| 3,732,652 | A | * | 5/1973 | Furgal | .................. | A47L 13/16 |
| | | | | | | 451/533 |
| 4,019,289 | A | * | 4/1977 | Korver | .................. | B24B 13/01 |
| | | | | | | 451/527 |
| 5,429,545 | A | * | 7/1995 | Meyer | .................. | A47L 13/17 |
| | | | | | | 451/523 |

(Continued)

FOREIGN PATENT DOCUMENTS

WO       2014167111 A1    10/2014

OTHER PUBLICATIONS

Combined Search and Examination Report issued in Application No. GB1506092.4 dated Sep. 15, 2015.

(Continued)

*Primary Examiner* — George B Nguyen
(74) *Attorney, Agent, or Firm* — Troutman Sanders LLP; Ryan Schneider; Chris Davis

(57) ABSTRACT

An abrasive sheet is described which is composed from a combination of an abrasive material and an abradable polymer composite wherein the abradable polymer composite comprises a layer of a first polymeric composition and conjoined thereto a layer of a second polymeric composition wherein the layer of said second polymeric composition is provided with a sensory cue.

25 Claims, 4 Drawing Sheets

(56) References Cited

U.S. PATENT DOCUMENTS

| | | | | |
|---|---|---|---|---|
| 5,733,176 A * | 3/1998 | Robinson | ................ | B24B 37/22 |
| | | | | 216/89 |
| 5,736,427 A * | 4/1998 | Henderson | .............. | B24B 37/20 |
| | | | | 156/345.13 |
| 5,779,519 A | 7/1998 | Oliver | | |
| 6,062,967 A * | 5/2000 | Calafut | ................... | A45D 29/04 |
| | | | | 132/73 |
| 6,090,475 A | 7/2000 | Robinson et al. | | |
| 6,190,746 B1 * | 2/2001 | Ishii | ....................... | B24D 11/00 |
| | | | | 428/40.1 |
| 6,423,078 B1 * | 7/2002 | Bays | ...................... | A61B 17/32 |
| | | | | 606/131 |
| 6,471,712 B2 * | 10/2002 | Burres | ................... | A45D 29/14 |
| | | | | 606/131 |
| 6,629,983 B1 * | 10/2003 | Ignon | ..................... | A61B 17/54 |
| | | | | 606/131 |
| 6,848,451 B2 * | 2/2005 | Postal | ...................... | A61C 1/07 |
| | | | | 132/75.8 |
| 7,153,311 B2 * | 12/2006 | Chung | ..................... | A61B 17/54 |
| | | | | 606/131 |
| 7,435,161 B2 * | 10/2008 | Prasad | ................... | B24B 37/205 |
| | | | | 451/41 |
| 7,442,113 B2 * | 10/2008 | Berman | .................. | B24B 37/22 |
| | | | | 451/41 |
| 7,581,545 B1 * | 9/2009 | Moldawski | ............ | A45D 40/22 |
| | | | | 132/73.6 |
| 8,118,644 B2 * | 2/2012 | Kulp | .................. | B24D 18/0009 |
| | | | | 451/41 |
| 8,430,721 B2 * | 4/2013 | Hsu | ........................ | B24B 37/22 |
| | | | | 451/533 |
| 8,851,058 B2 * | 10/2014 | Hoang | ................... | B24D 5/123 |
| | | | | 125/15 |
| 9,339,099 B2 * | 5/2016 | Yiu | ........................ | A61B 17/54 |
| 9,345,744 B2 * | 5/2016 | Gourdie | ................... | C07K 7/08 |
| 9,474,685 B2 * | 10/2016 | Thierman | .............. | A61H 39/08 |
| 9,491,997 B2 * | 11/2016 | Yiu | ........................ | A45D 29/05 |
| 9,901,724 B2 * | 2/2018 | Danenberg | ......... | A61M 37/0076 |
| 9,962,220 B2 * | 5/2018 | Domankevitz | .... | A61B 18/1402 |
| 10,006,216 B1 * | 6/2018 | Ronconi | ................ | E04H 4/1618 |
| 2002/0077037 A1 | 6/2002 | Tietz | | |
| 2003/0148614 A1 | 8/2003 | Simpson et al. | | |
| 2004/0214511 A1 | 10/2004 | Bermann et al. | | |
| 2007/0221238 A1 | 9/2007 | Tran | | |
| 2009/0151748 A1 | 6/2009 | Ridenhour | | |
| 2014/0109329 A1 | 4/2014 | Gummow et al. | | |
| 2016/0051283 A1 | 2/2016 | Runden et al. | | |

OTHER PUBLICATIONS

International Search Report and Written Opinion issued in International Application No. PCT/GB2016/051005 dated Jul. 22, 2016.

* cited by examiner

ABRASIVE SHEET

CROSS-REFERENCE TO RELATED APPLICATIONS

This application is a National Stage Entry of PCT Application No. PCT/GB2016/051005, filed 11 Apr. 2016, which claims priority to GB Application No. GB1506092.4, filed 10 Apr. 2015, the disclosures of each of which are herein incorporated by reference in their entirety.

BACKGROUND

The present invention is directed to an abradable material which can be used as an end of life indicator. In particular, the present invention is directed to an abradable material which can be used as an end of life indicator and is suitable for use with an abrasive material. The abradable material can be incorporated with the abrasive material into a dermabrasion device.

Dermabrasion devices for the removal of hard skin or calluses from the foot of an individual are known. Typically, such devices are in the form of a substrate to which is applied a dermabrasion material. In use the substrate is moved across the skin of a user and the dermabrasion material causes the hard skin or callus to be worn away. Such devices can be used for either medical or beauty purposes.

However, at the same time as abrading the skin the dermabrasion material can itself be worn away, can become less abrasive or can become clogged with the skin that has been removed so that in due course the substrate which carries the dermabrasion material has itself to be replaced in order that dermabrasion can continue to be carried out effectively.

However, for a number of reasons it can be difficult to determine when the abrasive material is no longer working efficiently.

BRIEF SUMMARY OF INVENTION

In one aspect, the invention is directed to an abrasive sheet comprising: an abrasive material; and an abradable polymer composite; wherein the abradable polymer composite comprises a first polymeric composition and a second polymeric composition; and wherein the second polymeric composition comprises a sensory cue.

In another aspect, the invention is directed to an abrasive sheet comprising: an abrasive material; and an abradable polymer composite comprising: a first polymeric composition comprising: 25-35 wt % of a co-polymer of styrene and isoprene; 50-60 wt % of a softener; 2-3 wt % of a first polymeric composition dispersant; and 12-13 wt % of a pigment; and a second polymeric composition comprising: 55-65 wt % of an SEBS co-polymer; 35-40 wt % of at least one pigment; 3-4 wt % of a second polymeric composition dispersant; and a sensory cue.

BRIEF DESCRIPTION OF THE FIGURES

The accompanying Figures, which are incorporated in and constitute a part of this specification, illustrate several aspects described below.

DETAILED DESCRIPTION OF INVENTION

Figure 1:
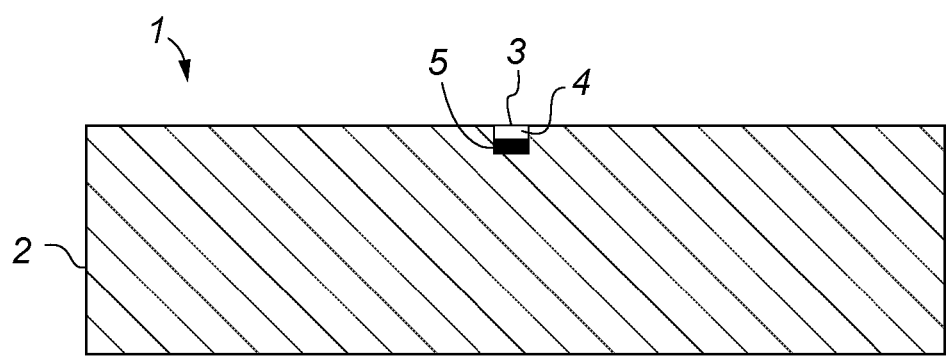
FIG. 1 illustrates a cross-section of an abrasive sheet in accordance with the first aspect of the present invention.

According to a first aspect of the present invention there is provided an abrasive sheet which comprises a combination of an abrasive material and an abradable polymer composite wherein the abradable polymer composite comprises a layer of a first polymeric composition and conjoined thereto a layer of a second polymeric composition wherein the layer of said second polymeric composition is provided with a sensory cue.

The abrasive material and the abradable polymer composite are arranged in such a way that in use the layer of the first polymeric composition of the abradable polymer composite is itself abraded on contact with the surface which is abraded by the abrasive material. Abrasion of the layer of the first polymeric composition exposes the sensory cue of the second polymeric composition to a user.

The first polymeric composition and the second polymeric composition can comprise the same polymer or a different polymer. The first polymeric composition is typically softer than the second polymer composition. For example, the first polymeric composition can include a softening agent which is not present in the second polymeric composition.

In a preferred embodiment the first polymeric composition comprises a first polymer and the second polymeric composition comprises a second different polymer.

Typically, the sensory cue becomes visible/exposed after at least 50% of the layer of the first polymeric composition has been abraded. Typically, the sensory cue becomes visible/exposed after at least 75% of the layer of the first polymeric composition has been abraded. More typically, the sensory cue becomes visible/exposed after at least 85% of the layer of the first polymeric composition has been abraded.

Preferably the sensory cue is in the form of a visual indicator. In an alternative embodiment, the sensory cue can be in the form of an olfactory indicator, such as a fragrance. Any suitable fragrance or perfume can be used. Preferred fragrances are bergamot and eucalyptus.

The fragrance or perfume can be included in the polymeric material at a level of 0.05-5 wt %. Typically, the fragrance or perfume can be included in the polymeric material at a level of 1-2 wt %.

Typically, the visual indicator is in the form of a colour. In an alternative embodiment the visual indicator can be in the form of a word or image. In a preferred embodiment, the layer of the first polymeric material is of a first colour and the layer of the second polymeric material is of a second colour.

In an alternative embodiment, the colour of the layer of the second polymeric composition can change after a predetermined period of exposure to light.

The visual indicator is evenly distributed throughout the second polymeric composition. For example, the visual indicator can be provided on the second polymeric composition as at least one strip that traverses the surface of the second layer. Alternatively, the visual indicator can be provided in discreet portions.

Typically, the polymer of the first polymeric composition is selected from an elastomer, a rubber, a silicone or mixtures thereof. More typically, the polymer of the first polymeric composition is made of a co-polymer of polymethacrylate, a water based styrene-acrylic resin, a waterbased polyurethane resin, polyvinyl chloride, an acrylic resin, an ethylene-vinyl acetate co-polymer, a styrene-butadiene co-polymer, a styrene-butadiene-styrene co-polymer, a styrene-isoprene-styrene co-polymer.

A preferred the polymer of the first polymeric composition is a styrene-isoprene-styrene co-polymer having a styrene content of 10-30%. A more preferred polymer of the first polymeric composition is a styrene-isoprene-styrene co-polymer having a styrene content of 12-20%. A most preferred polymer of the first polymeric composition is a styrene-isoprene-styrene co-polymer having a styrene content of 15-17%.

The polymer of the first polymeric composition can be a block co-polymer or a random co-polymer. Typically, the co-polymer comprises different blocks in the polymer backbone. Typical block co-polymer will be an AB type block co-polymer or an ABA type block co-polymer.

The polymer of the first polymeric composition can be linear, branched or a higher order geometry such as star co-polymer.

The layer of the first polymeric composition can comprise one or more additional components such as softeners, fillers, plasticisers, dispersants and pigments.

The incorporation of components such as softeners, fillers, plasticisers can adjust the properties of the first polymeric composition to achieve the desired level of abradability. In addition, incorporation of a cross-linking agent, or changing the glass-transition temperature of the material can also change the properties of the first polymeric composition. The abradability of the first polymeric composition can be increased by the addition of one or more plasticisers which are able to swell and/or soften the polymer matrix. A typical example of a plasticiser suitable for use with a styrene block copolymer is an aliphatic hydrocarbon such as a mineral oil. The abradability of the first polymeric composition can be reduced by the addition of a filler or fibre reinforcement material. Typical fillers include talc or mica, silica, wollastonite, glass beads, calcium carbonate, mineral fibres and carbon fibres.

Alternatively, the use of a styrene-based material which has a higher styrene content will result in the first polymeric composition having a higher hardness and/or resistance to abrasion.

Typically, the layer of the first polymeric composition can comprise up to 60 wt % of the first polymer. More typically, the layer of the first polymeric composition can comprise up to 40 wt % of the first polymer. Typically, the layer of the first polymeric composition can comprise at least 20 wt % of the first polymeric material. More typically, the layer of the first polymeric composition can comprise at least 25 wt % of the first polymeric material.

In a preferred embodiment the first polymer is present at a level of between 20 wt % and 60 wt %. Preferably the first polymer is present at a level of between 25 wt % and 40 wt %.

The one or more plasticisers can be present in the first polymeric composition at a level of at least 40 wt %. Typically, the one or more plasticisers are present in the first polymeric composition at a level of at least 50 wt %. The one or more excipients can be present in the first polymeric composition at a level of up to 75 wt %. Typically, the one or more excipients are present in the first polymeric composition at a level of up to 60 wt %.

In a preferred embodiment the one or more plasticisers are present in the first polymeric composition at a level of between 40 wt % and 75 wt %. Preferably the one or more excipients are present in the first polymeric composition at a level of between 50 wt % and 60 wt %.

The ratio of the first polymer and the one or more plasticisers can be in the range of 1:1 to 1:2.5. A preferred ratio is in the range of 1:1.2 and 1:2. A more preferred ratio is in the range of 1:1.5 to 1:1.9.

In the context of the present invention, the term 'abradability' refers to the potential for the first and second polymeric compositions to be abraded in use. A higher level of abradability indicates that the material is itself readily abraded. A higher level of abradability corresponds to a lower resistance to abrasion. Conversely, a lower level of abradability indicates that the material itself is not readily abraded and has a higher resistance to abrasion. In general, the softer a material is the higher its abradability will be.

The polymer of the first polymeric composition can be selected to have a Shore A hardness of up to about 60. Typically, the polymer of the first polymeric composition can have a Shore A hardness of about 10 to about 50. More typically, the polymer of the first polymeric composition can have a Shore A hardness of 20-30. Most typically, the polymer of the first polymeric composition can have a Shore A hardness of 25.

The first polymeric composition can be further provided with a dispersant. The dispersant can be selected from an alkylammonium salt of a polymer having at least one acidic group. Other examples of dispersants include polyacrylates, polyurethanes and long-chain fatty acids functionalised with either ionic or non-ionic end-groups.

The dispersant is typically present in the first polymeric composition at a level of at least 0.5 wt %, preferably at least 1 wt %, more preferably 2.5 wt %. The dispersant is typically present in the first polymeric composition at a level of up to 5 wt %, preferably up to 4 wt %, more preferably up to 3.5 wt %. The dispersant can be present at a level of 0.5-5 wt %, preferably the dispersant can be present at a level of 1-4 wt %, more preferably the dispersant can be present at a level of 2.5-3.5 wt %.

The colour of the first polymeric composition can be selected to be a pigment of any suitable colour which has low opacity. The pigment can be selected to be carbon black.

The colourant is typically present in the first polymeric composition at a level of at least 5 wt %, preferably at least 10 wt %, more preferably 12.5 wt %. The colourant is typically present in the first polymeric composition at a level of up to 25 wt %, preferably up to 20 wt %, more preferably up to 15 wt %. The colourant can be present at a level of 5-25 wt %, preferably the colourant can be present at a level of 10-20 wt %, more preferably the colourant can be present at a level of 12.5-15 wt %.

The first polymeric composition can further include an additive selected from shea butter, grape seed oil. The additive can be selected from any suitable fragrance or perfume.

The polymer of the second polymeric composition can be selected from the group consisting of polyurethane, a styrene ethylene butylene styrene co-polymer, natural rubber, acrylic rubber, polyolefin elastomer, ethylene-vinyl acetate copolymers, ionomers of ethylene and acid functional monomers. A preferred polymer of the second polymeric composition is a styrene ethylene butylene styrene co-polymer on to which is grafted maleic anhydride. The polymer of the second polymeric composition should be selected to have good adhesion to the top layer.

Typically, the second polymeric composition can comprise up to 65 wt % of the second polymer. More typically, the layer of the second polymeric composition can comprise up to 60 wt % of the second polymer. Typically, the second polymeric composition can comprise at least 50 wt % of the second polymer. More typically, second polymeric composition can comprise at least 55 wt % of the second polymer.

In a preferred embodiment the second polymer is present at a level of between 50 wt % and 65 wt %. Preferably the second polymer is present at a level of between 55 wt % and 60 wt %.

Typically, the second polymeric composition is harder or less abradable than the first polymeric composition. The polymer of the second polymeric composition can be selected to have a Shore A hardness of between 40 and 100. Preferably the polymer of the second polymeric composition can be selected to have a Shore A hardness of between 50 and 90. More preferably the polymer of the second polymeric composition can be selected can be selected to have a Shore A hardness of between 65 and 75. Most preferably polymer of the second polymeric composition can be selected can be selected to be a Shore A hardness of about 70.

The polymer of the second polymeric composition can be a block co-polymer or a random co-polymer. Typically, the co-polymer comprises different blocks in the polymer backbone. Typical block co-polymer will be an AB type block co-polymer or an ABA type block co-polymer.

The polymer of the second polymeric composition can be linear, branched or a higher order geometry such as star co-polymer.

The second polymeric composition can be further provided with a dispersant. The dispersant can be selected from an alkylammonium salt of a polymer having at least one acidic group.

Other examples of dispersants include polyacrylates, polyurethanes and long-chain fatty acids functionalised with either ionic or non-ionic end-groups.

The dispersant is typically present in the second polymeric composition at a level of at least 0.1 wt %, preferably at least 3 wt %. The dispersant is typically present in the second polymeric composition at a level of up to 5 wt %. The dispersant can be present at a level of 0.1-5 wt %, preferably the dispersant can be present at a level of 3-5 wt %, more preferably the dispersant can be present at a level of 3-4 wt %.

The colour of the second polymeric composition can be selected to be at least one pigment of any suitable colour. The colour is selected to provide a contrast with the colour of the first polymeric material. The pigment can be selected to be yellow, white or a combination thereof.

The colourant is typically present in the second polymeric composition at a level of at least 30 wt %, preferably at least 40 wt %. The colourant is typically present in the second polymeric composition at a level of up to 45 wt %, preferably up to 40 wt %. The colourant can be present at a level of 30-45 wt %, preferably the colourant can be present at a level of 35-40 wt %.

In a preferred embodiment the abradable polymer composite comprises a layer of a first polymeric composition comprising a co-polymer of styrene and isoprene, a softener and a dispersant, and a layer of a second polymeric composition comprising a SEBS co-polymer, at least one pigment and a dispersant.

In a particularly preferred embodiment, the abradable polymer composite comprises a layer of a first polymeric composition comprising a 25-35 wt % of a co-polymer of styrene and isoprene, 50-60 wt % of a softener and 2-3 wt % of a dispersant and 12-13 wt % of a pigment; and a layer of a second polymeric composition comprising 55-65 wt % of a SEBS co-polymer, 35-40 wt % of at least one pigment and 3-4 wt % of a dispersant.

Preferably the abradable polymer composite comprises up to 20% of the surface area of the abrasive sheet available for dermabrasion. More preferably the abradable composite comprises 10-15% of the surface area of the abrasive sheet available for dermabrasion.

The abradable polymer composite can be provided on the abrasive sheet in the form of at least one transverse strip. The strip can have a width of up to 1 cm. In a preferred embodiment the width of the at least one transverse strip is 1-5 mm. In alternative embodiments, the abradable composition is provided on the material as a diagonal strip, vertical strip or as discreet portions.

In an alternative embodiment, the abradable polymer composition can be provided as one or more discreet portions proximate the abradasive material. The discreet portions can be in any suitable shape such as a triangle, circle or square or in the form of a logo.

Typically, the edge of the one or more discreet portions of the abradable polymer composition contacts the abrasive material.

The abradable polymer composite can be provided with a polyurethane 'primer' which is located on the surface of the second polymer composition opposite the surface which has the first polymer composition applied thereto. The 'primer' is a material that provides a layer between the abradable polymer composite and the surface to which it is applied to enable adhesion between the composite and the surface to which it is applied. In an alternative embodiment the abradable polymer composition is provided with a base coat on the surface of the second polymer composition opposite to that on which the first polymer composition is provided. The base coat provides improved adhesion of the second polymer composition to the surface to which it is applied. The base coat comprises a polymeric material selected from the group consisting of polyurethane, a styrene ethylene butylene styrene co-polymer natural rubber, acrylic rubber, polyolefin elastomer, ethylene-vinyl acetate copolymers, ionomers of ethylene and acid functional monomers. A preferred material for the base coat is a styrene ethylene butylene styrene co-polymer on to which is grafted maleic anhydride.

The abrasive sheet can be provided with additional abrasive materials such as diamond fragments/particles or pumice.

Typically the abrasive sheet has a thickness of 200-300 microns. The layer of the first polymer composition has a thickness of 150-200 microns and the layer of the second polymer composition has a thickness of 50-100 microns. Additional layers can have a thickness of up to 50 microns If the third layer provides an outer coating then the thickness is preferably up to 50 microns, preferably 10-30 microns.

The ratio of the thickness of the layer of the first polymer composition and the thickness of the layer of the second polymer composition can be from 1:1 to 1:4. A preferred ratio range is 1:2 to 1:3.

The layer of the first polymer composition typically wears to expose the colour of the layer of the second polymer composition in a period of 5 mins to 5 hrs. Preferably the period is from 30 mins to 3 hrs. More preferably the period is from 45 to 90 mins.

According to a second aspect of the present invention there is provided a dermabrasion device which comprises a support that is provided with the abrasive sheet of the first aspect of the present invention.

The support is preferably made of an acrylonitrile-butadiene-styrene co-polymer.

Typically the dermabrasion device is in the form of a drum. The drum can be shaped such that the abrasive surface is in the form of a convex curve such that the diameter of the drum is greater in the middle than at either end.

Typically, the surface of the drum is in the form of a parabolic arc. Typically the length of the drum is between 2 and 4 times greater than the diameter of the drum. More typically the length of the drum is between 2 and 3 times greater than the diameter of the drum. Most typically, the length of the drum is 2.5 times greater than the diameter of the drum at its widest. Preferably, the drum is in the shape of a barrel. A more preferred shape is that of an elongated barrel.

Preferably, the diameter at the centre of the drum is between 10% and 30% larger than the diameter at the ends of the drum. More preferably, the diameter at the centre of the drum is between 15% and 25% larger than the diameter at the ends of the drum. More preferably, the diameter at the centre of the drum is between 20% and 22% larger than the diameter at the ends of the drum.

Typically, at least 80% of the surface area of the drum is used in the dermabrasion process. More typically, at least 85% of the surface area of the drum is used in the dermabrasion process. Even more typically, at least 90% of the surface area of the drum is used in the dermabrasion process.

The material which forms the abrasive surface of the drum can be selected to provide the desired level of abrasiveness. For example, the abrasive surface can be made of a coarse material if a high level of abrasiveness is required, or can be made of a fine material if a low level of abrasiveness is required.

According to a third aspect of the present invention there is provide a use of the abrasive sheet of the first aspect or the use of dermabrasion device of the second aspect for the removal of hard skin or callus from an individual.

According to a fourth aspect of the present invention there is provided a polymer composite which comprises a layer of a first polymeric composition and conjoined thereto a layer of a second polymeric composition wherein the layer of said second polymeric composition is provided with sensory cue.

The first polymeric composition and the second polymeric composition can comprise the same polymer or a different polymer. If the first polymeric composition and the second polymeric composition comprise the same polymer then the properties of first polymeric composition are altered so that said first polymeric composition is softer than the second polymer composition. For example, the first polymeric composition can include a softening agent which is not present in the second polymeric composition.

In a preferred embodiment the first polymeric composition comprises a first polymer and the second polymeric composition comprises a second different polymer.

Typically, the sensory cue becomes visible/exposed after at least 50% of the layer of the first polymeric composition has been abraded. Typically, the sensory cue becomes visible/exposed after at least 75% of the layer of the first polymeric composition has been abraded. More typically, the sensory cue becomes visible/exposed after at least 85% of the layer of the first polymeric composition has been abraded.

Preferably the sensory cue is in the form of a visual indicator. In an alternative embodiment, the sensory cue can be in the form of an olfactory indicator, such as a fragrance. Any suitable fragrance or perfume can be used. Preferred fragrances are bergamot and eucalyptus.

The fragrance or perfume can be included in the polymeric material at a level of 1-2 wt %.

Typically, the visual indicator is in the form of a colour. In an alternative embodiment the visual indicator can be in the form of a word or image. In a preferred embodiment, the layer of the first polymeric material is of a first colour and the layer of the second polymeric material is of a second colour.

In an alternative embodiment, the colour of the layer of the second polymeric composition can change after a predetermined period of exposure to light.

The visual indicator is evenly distributed throughout the second polymeric composition. For example, the visual indicator can be provided on the second polymeric composition as at least one strip that traverses the surface of the second layer. Alternatively, the visual indicator can be provided in discreet portions.

Typically, the polymer of the first polymeric composition is selected from an elastomer, a rubber, a silicone or mixtures thereof. More typically, the polymer of the first polymeric composition is made of a co-polymer of polymethacrylate, a water based styrene-acrylic resin, a water based polyurethane resin, polyvinyl chloride, an acrylic resin, an ethylene-vinyl acetate co-polymer, a styrene-butadiene co-polymer, a styrene-butadiene-styrene co-polymer, a styrene-isoprene-styrene co-polymer.

A preferred the polymer of the first polymeric composition is a styrene-isoprene-styrene co-polymer having a styrene content of 10-30%. A more preferred polymer of the first polymeric composition is a styrene-isoprene-styrene co-polymer having a styrene content of 12-20%. A most preferred the polymer of the first polymeric composition is a styrene-isoprene-styrene co-polymer having a styrene content of 15-17%.

The polymer of the first polymeric composition can be a block co-polymer or a random co-polymer. Typically, the co-polymer comprises different blocks in the polymer backbone. Typical block co-polymer will be an AB type block co-polymer or an ABA type block co-polymer.

The polymer of the first polymeric composition can be linear, branched or a higher order geometry such as star co-polymer.

The co-polymer can be linear, branched or a higher order geometry such as star co-polymer.

The first polymer composition can comprises additional components such as softeners, fillers, plasticisers, dispersants and pigments.

The incorporation of components such as softeners, fillers, plasticisers can adjust the properties of the first polymeric composition to achieve the desired level of abradability. In addition, incorporation of a cross-linking agent, or changing the glass-transition temperature of the material can also change the properties of the first polymeric composition. The abradability of the first polymeric composition can be increased by the addition of one or more plasticisers which are able to swell and/or soften the polymer matrix. A typical example of a plasticiser is an aliphatic hydrocarbon such as a mineral oil. The abradability of the first polymeric composition can be reduced by the addition of a filler or fibre reinforcement material. Typical fillers include talc or mica, silica, wollastonite, glass beads, calcium carbonate, mineral fibres and carbon fibres.

Alternatively, the use of a styrene-based material which has a higher styrene content will result in the first polymeric composition having a higher hardness and/or resistance to abrasion.

Typically, the layer of the first polymeric composition can comprise up to 60 wt % of the first polymer. More typically, the layer of the first polymeric composition can comprise up to 40 wt % of the first polymer. Typically, the layer of the first polymeric composition can comprise at least 20 wt % of the first polymeric material. More typically, the layer of the first polymeric composition can comprise at least 25 wt % of the first polymeric material.

In a preferred embodiment the first polymer is present at a level of between 20 wt % and 50 wt %. Preferably the first polymer is present at a level of between 25 wt % and 40 wt %.

The one or more plasticisers can be present in the first polymeric composition at a level of at least 40 wt %. Typically, the one or more plasticisers are present in the first polymeric composition at a level of at least 50 wt %. The one or more excipients can be present in the first polymeric composition at a level of up to 75 wt %. Typically, the one or more excipients are present in the first polymeric composition at a level of up to 60 wt %.

In a preferred embodiment the one or more plasticisers are present in the first polymeric composition at a level of between 40 wt % and 75 wt %. Preferably the one or more excipients are present in the first polymeric composition at a level of between 50 wt % and 60 wt %.

The ratio of the first polymer and the one or more plasticisers can be in the range of 1:1 to 1:2.5. A preferred ratio is in the range of 1:1.2 and 1:2. A more preferred ratio is in the range of 1:1.5 to 1:1.9.

The polymer of the first polymeric composition can be selected to have a Shore A hardness of up to about 60. Typically, the polymer of the first polymeric composition can have a Shore A hardness of about 10 to about 50. More typically, the polymer of the first polymeric composition can have a Shore A hardness of 20-30. Most typically, the polymer of the first polymeric composition can have a Shore A hardness of 25.

The first polymeric composition can be further provided with a dispersant. The dispersant can be selected from an alkylammonium salt of a polymer having at least one acidic group. Other examples of dispersants include polyacrylates, polyurethanes and long-chain fatty acids functionalised with either ionic or non-ionic end-groups.

The dispersant is typically present in the first polymeric composition at a level of at least 0.5 wt %, preferably at least 1 wt %, more preferably 2.5 wt %. The dispersant is typically present in the first polymeric composition at a level of up to 5 wt %, preferably up to 4 wt %, more preferably up to 3.5 wt %. The dispersant can be present at a level of 0.5-5 wt %, preferably the dispersant can be present at a level of 1-4 wt %, more preferably the dispersant can be present at a level of 2.5-3.5 wt %.

The colour of the first polymeric composition can be selected to be a pigment of any suitable colour which has low opacity. The pigment can be selected to be carbon black.

The colourant is typically present in the first polymeric composition at a level of at least 5 wt %, preferably at least 10 wt %, more preferably 12.5 wt %. The colourant is typically present in the first polymeric composition at a level of up to 25 wt %, preferably up to 20 wt %, more preferably up to 15 wt %. The colourant can be present at a level of 5-25 wt %, preferably the colourant can be present at a level of 10-20 wt %, more preferably the colourant can be present at a level of 12.5-15 wt %.

The first polymeric composition can further include an additive selected from shea butter, grape seed oil.

The polymer of the second polymeric composition can be selected from the group consisting of polyurethane, a styrene ethylene butylene styrene co-polymer, natural rubber, acrylic rubber, polyolefin elastomer, ethylene-vinyl acetate copolymers, ionomers of ethylene and acid functional monomers. A preferred polymer of the second polymeric composition is a styrene ethylene butylene styrene co-polymer on to which is grafted maleic anhydride. The polymer of the second polymeric composition should be selected to have good adhesion to the top layer.

Typically, the second polymeric composition can comprise up to 65 wt % of the second polymer. More typically, the layer of the second polymeric composition can comprise up to 60 wt % of the second polymer. Typically, the second polymeric composition can comprise at least 50 wt % of the second polymer. More typically, second polymeric composition can comprise at least 55 wt % of the second polymer.

In a preferred embodiment the second polymer is present at a level of between 50 wt % and 65 wt %. Preferably the second polymer is present at a level of between 55 wt % and 60 wt %.

Typically, the second polymeric composition is harder or less abradable than the first polymeric composition. The polymer of the second polymeric composition can be selected to have a Shore A hardness of between 40 and 100. Preferably the polymer of the second polymeric composition can be selected to have a Shore A hardness of between 50 and 90. More preferably the polymer of the second polymeric composition can be selected can be selected to have a Shore A hardness of between 65 and 75. Most preferably polymer of the second polymeric composition can be selected can be selected to be a Shore A hardness of about 70.

The polymer of the second polymeric composition can be a block co-polymer or a random co-polymer. Typically, the co-polymer comprises different blocks in the polymer backbone. Typical block co-polymer will be an AB type block co-polymer or an ABA type block co-polymer.

The polymer of the second polymeric composition can be linear, branched or a higher order geometry such as star co-polymer.

The second polymeric composition can be further provided with a dispersant. The dispersant can be selected from an alkylammonium salt of a polymer having at least one acidic group.

The dispersant is typically present in the second polymeric composition at a level of at least 0.1 wt %, preferably at least 3 wt %. The dispersant is typically present in the second polymeric composition at a level of up to 5 wt %. The dispersant can be present at a level of 0.1-5 wt %, preferably the dispersant can be present at a level of 3-5 wt %, more preferably the dispersant can be present at a level of 3-4 wt %.

The colour of the second polymeric composition can be selected to be at least one pigment of any suitable colour. The colour is selected to provide a contrast with the colour of the first polymeric material. The pigment can be selected to be yellow, white or a combination thereof.

The colourant is typically present in the second polymeric composition at a level of at least 30 wt %, preferably at least 40 wt %. The colourant is typically present in the second polymeric composition at a level of up to 45 wt %, preferably up to 40 wt %. The colourant can be present at a level of 30-45 wt %, preferably the colourant can be present at a level of 35-40 wt %.

In a preferred embodiment the polymer composite comprises a layer of a first polymeric composition comprising a co-polymer of styrene and isoprene, a softener and a dispersant, and a layer of a second polymeric composition comprising a SEBS co-polymer, at least one pigment and a dispersant.

In a particularly preferred embodiment, the polymer composite comprises a layer of a first polymeric composition comprising a 25-35 wt % of a co-polymer of styrene and isoprene, 50-60wt % of a softener and 2-3 wt % of a dispersant and 12-13 wt % of a pigment; and a layer of a second polymeric composition comprising 55-65 wt % of a SEBS co-polymer, 35-40 wt % of at least one pigment and 3-4 wt % of a dispersant.

The polymer composite can be provided with a polyurethane 'primer' which is located on the surface of the second polymer composition opposite the surface which has the first polymer composition applied thereto. The 'primer' is a material that provides a layer between the abradable polymer composition and the surface to which it is applied to enable adhesion between the composite and the surface. In an alternative embodiment the polymer composite is provided with a base coat on the surface material of the second polymer composition opposite to that on which the first polymer composition is provided. The base coat provides improved adhesion of the second polymer composition to the surface to which it is applied. The base coat comprises a polymeric material selected from the group consisting of polyurethane, a styrene ethylene butylene styrene co-polymer natural rubber, acrylic rubber, polyolefin elastomer, ethylene-vinyl acetate copolymers, ionomers of ethylene and acid functional monomers. A preferred material for the base coat is a styrene ethylene butylene styrene co-polymer grafted with maleic anhydride.

The polymer composite can be provided with additional layers of material. Typically, the polymer composition can be provided with up to 3 additional layers. More typically, the polymer composition is provided with one additional layer. The additional layers can comprise quartz, grain, or diamond particles.

Typically the polymer composite has a thickness of 200-300 microns. The first layer of the first polymeric composition has a thickness of 150-200 microns and the layer of the second polymer composition has a thickness of 50-100 microns. Additional layers can have a thickness of up to 50 microns If the third layer provides an outer coating then the thickness is preferably up to 50 microns, preferably 10-30 microns.

The ratio of the thickness of the layer of the first polymer composition and the thickness of the layer of the second polymer composition can be from 1:1 to 1:4. A preferred ratio range is 1:2 to 1:3.

Figure 2:
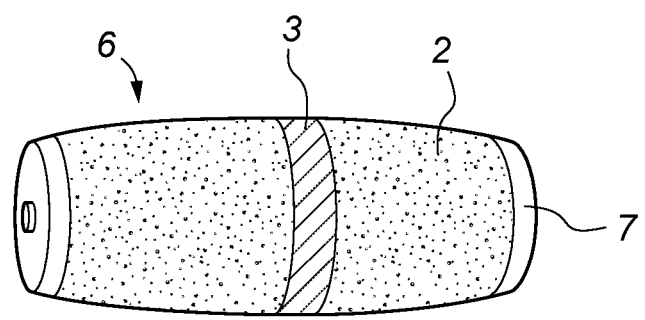
FIG. 2 illustrates a dermabrasion device in accordance with the second aspect of the present invention prior to use.
Figure 3:
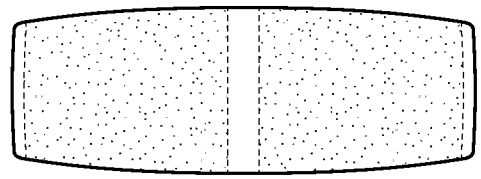
FIG. 3 illustrates the dermabrasion device of FIG. 2 after the first layer of the abradable composition has worn away.
Figure 4:
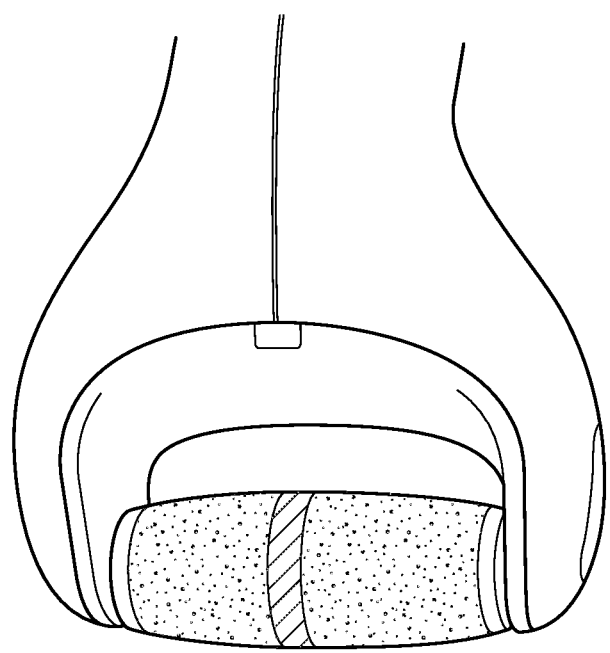
FIG. 4 illustrates the head of apparatus which holds the dermabrasion device in use.

Example embodiments of an abrasive composition and its incorporation into a dermabrasion device in accordance with the present invention will now be described with reference to the accompanying Figures in which:

FIG. 1 illustrates a cross-section of an abrasive sheet in accordance with the first aspect of the present invention;

FIG. 2 illustrates a dermabrasion device in accordance with the second aspect of the present invention prior to use;

FIG. 3 illustrates the dermabrasion device of FIG. 2 after the first layer of the abradable composition has worn away; and FIG. 4 illustrates the head of apparatus which holds the dermabrasion device in use.

Referring to FIG. 1, an abrasive sheet is generally depicted at 1. The abrasive sheet 1 comprises an abrasive material 2 and an abradable polymer composite 3. The abradable polymer composite 3 comprises a first polymeric composition 4 having a first colour, and a second polymeric composition 5 having a second colour.

Referring to FIG. 2, there is generally depicted a dermabrasion device at 6. The device 6 is in the form of a barrel. The device 6 comprises a substrate (not shown), the abradable polymer composite 3 and the abrasive material 2. The abradable composite 3 is provided as a strip of material round the circumference of the barrel. The abradable composite 3 and the abrasive material 2 are fixed to the substrate (not shown) using an adhesive or a primer (not shown). The abrasive material 2 comprises silicon carbide. The dermabrasion device 6 is provided with an axle (not shown) about which the device rotates when in use. A cap 7 is provided at both ends to support the axle.

FIG. 3 illustrates the dermabrasion device of FIG. 2 after the first layer of the abradable composition has worn away. As can be seen the colours of the first and second polymer compositions are different. FIG. 4 illustrates the head of apparatus which holds the dermabrasion device in use. In the embodiment shown in FIG. 4, the device has yet to be used for dermabrasion.

An example of both the first and second polymer composition which form the abradable polymer composition is shown below:

First Polymer Composition:

| Material | Wt % |
| --- | --- |
| Poly(styrene-isoprene-styrene) (SIS) | 29.26 |
| Activated carbon | 13.36 |
| Mineral oil | 54.85 |
| Alkylammonium salt | 2.53 |
| Total | 100 |

Second Polymer Composition:

| Material | Wt % |
| --- | --- |
| SEBS grafted with maleic anhydride | 59.24 |
| Titanium Dioxide | 18.53 |
| Dye | 18.53 |
| Alkylammonium salt | 3.70 |
| Total | 100 |

The first and second polymer compositions can be made using standard polymer synthetic methodology known to the man skilled in the art.

If the abradable polymer composite is applied to the dermabrasion device using an adhesive, prior to application of the device is masked either side of the area to be coated. The adhesive is applied as a solution of SEBS modified maleic anhydride in toluene in two thin coats. The coating is dried between and after the two coats at about 100° C. for 1-2 minutes. The second polymer composition is applied to the base coat as a solution in toluene immediately after drying the adhesive layer. The second polymer composition is dried at about 100° C. for 1-2 minutes. The first polymer composition is applied in the same way as the previous coats. The dermabrasion device is then oven dried at 50° C. for 48 hours to remove residual toluene.

An advantage of the present invention is that there is provided a dermabrasion device which provides a user an indication when said device has reached the end of its useful life.

Further modifications and improvements can be made without departing from the scope of the invention described herein.

The invention claimed is:

1. A drum for a dermabrasion device having an abrasive surface comprising:
   an abrasive material for abrading the skin of a user; and
   an abradable polymer composite;
   wherein the abradable polymer composite comprises a first polymeric composition and a second polymeric composition; and
   wherein the second polymeric composition comprises a sensory cue.

2. The drum as claimed in claim 1, wherein the first polymeric composition is in the form of a layer;
   wherein the second polymeric composition is in the form of a layer conjoined to the layer of the first polymeric composition;
   wherein the abrasive material and the abradable polymer composite are arranged in such a way that in use, the layer of the first polymeric composition of the abradable polymer composite is itself abraded on contact with a surface which is abraded by the abrasive material.

3. The drum as claimed in claim 2, wherein abrasion of the layer of the first polymeric composition exposes the sensory cue of the second polymeric composition to a user.

4. The drum as claimed in claim 2, wherein the sensory cue becomes visible/exposed after at least 50% of the layer of the first polymeric composition has been abraded.

5. The drum as claimed in claim 2, wherein the sensory cue is in the form of a visual indicator.

6. The drum as claimed in claim 5, wherein the visual indicator is in the form of a color.

7. The drum as claimed in claim 2, wherein the polymer of the layer of the first polymeric composition is selected from the group consisting of an elastomer, a rubber, a silicone and mixtures thereof.

8. The drum as claimed in claim 2, wherein the polymer of the layer of the first polymeric composition is selected from the group consisting of those made of a co-polymer of polymethacrylate, a water based styrene-acrylic resin, a water-based polyurethane resin, polyvinyl chloride, an acrylic resin, an ethylene-vinyl acetate co-polymer, a styrene-butadiene co-polymer, a styrene-butadiene-styrene co-polymer, and a styrene-isoprene-styrene co-polymer.

9. The drum as claimed in claim 2, wherein the polymer of the layer of the first polymeric composition is a styrene-isoprene-styrene co-polymer having a styrene content of between 10-30%.

10. The drum as claimed in claim 2, wherein the layer of the first polymeric composition comprises one or more additional components;
    wherein the incorporation of the one or more additional components adjusts properties of the first polymeric composition to achieve a desired level of abradability.

11. The drum as claimed in claim 10, wherein the polymer of the layer of the first polymeric composition comprises up to 60 wt % of the first layer of the first polymeric composition.

12. The drum as claimed in claim 10, wherein the one or more additional components comprises one or more plasticisers that are present in the layer of the first polymeric composition at a level of at least 40 wt %.

13. The drum as claimed in claim 12, wherein the ratio of the polymer of the layer of the first polymeric composition to the one or more plasticisers is in the range of between 1:1 to 1:2.5.

14. The drum as claimed in claim 2, wherein the polymer of the layer of the first polymeric composition is selected to have a Shore A hardness of up to about 60.

15. The drum as claimed in claim 2, wherein the polymer of the layer of the second polymeric composition is selected from the group consisting of polyurethane, a styrene ethylene butylene styrene co-polymer, natural rubber, acrylic rubber, polyolefin elastomer, ethylene-vinyl acetate copolymers, ionomers of ethylene and acid functional monomers.

16. The drum as claimed in claim 15, wherein the layer of the second polymeric composition comprises up to 65 wt % of the polymer of the layer of the second polymeric composition.

17. The drum as claimed in claim 2, wherein the second polymeric composition is harder or less abradable than the first polymeric composition.

18. The drum as claimed in claim 17, wherein the polymer of the layer of the second polymeric composition is selected to have a Shore A hardness of between 40 and 100.

19. The drum as claimed in claim 2, wherein the layer of the first polymeric composition comprises a co-polymer of styrene and isoprene, a softener and a dispersant; and
    wherein the layer of the second polymeric composition comprises an SEBS co-polymer, at least one pigment and a dispersant.

20. An abrasive sheet comprising:
    an abrasive material; and
    an abradable polymer composite comprising:
      a first polymeric composition comprising:
        25-35 wt % of a co-polymer of styrene and isoprene;
        50-60 wt % of a softener;
        2-3 wt % of a first polymeric composition dispersant; and
        12-13 wt % of a pigment; and
      a second polymeric composition comprising
        55-65 wt % of an SEBS co-polymer;
        35-40 wt % of at least one pigment;
        3-4 wt % of a second polymeric composition dispersant; and
      a sensory cue.

21. The abrasive sheet as claimed in claim 20, wherein the abradable polymer composite comprises up to 20% of the surface area of the abrasive sheet available for dermabrasion.

22. The abrasive sheet as claimed in claim 20, wherein the abrasive sheet has a thickness of between 200-300 microns.

23. The abrasive sheet as claimed in claim 20 further comprising a polyurethane primer;
    wherein the first polymeric composition is in the form of a layer;
    wherein the second polymeric composition is in the form of a layer conjoined to the layer of the first polymeric composition;
    wherein the polyurethane primer is located on the surface of the layer of the second polymer composition opposite the surface of the layer of the second polymer composition that has the first polymer composition conjoined thereto;
    wherein the polyurethane primer provides a layer between the abradable polymer composite and a surface to which it is applied to enable adhesion between the abradable polymer composite and the surface to which it is applied.

24. The abrasive sheet as claimed in claim 23, wherein the ratio of the thickness of the layer of the first polymer composition to the thickness of the layer of the second polymer composition is from between 1:1 to 1:4.

25. The abrasive sheet as claimed in claim 23, wherein in use, the layer of the first polymer composition wears to expose the color of the layer of the second polymer composition in a period of between 5 mins to 5 hrs.

* * * * *